United States Patent [19]
Sugiyama

[11] Patent Number: 5,720,474
[45] Date of Patent: Feb. 24, 1998

[54] SHOCK ABSORBING MECHANISM OF DISPLACEMENT FOR STICK, LEG, ETC.

[76] Inventor: Kazuo Sugiyama, 8-20, 3-chome, Sakurajosui, Setagaya-ku, Tokyo, Japan

[21] Appl. No.: 624,351

[22] Filed: Apr. 3, 1996

[30] Foreign Application Priority Data

Apr. 17, 1995 [JP] Japan ................... 7-090880
Feb. 7, 1996 [JP] Japan ................... 8-021384

[51] Int. Cl.$^6$ ................... B60G 11/14
[52] U.S. Cl. ................... 267/249; 267/153; 135/75
[58] Field of Search ................... 267/33, 152, 153, 267/174, 249, 287, 201, 169, 292, 34, 35, 202, 219, 121; 280/819, 821, 822, 823; 623/27; 135/35, 75, 77, 82

[56] References Cited

U.S. PATENT DOCUMENTS

| | | | |
|---|---|---|---|
| 2,549,037 | 4/1951 | Withall | 267/202 |
| 4,010,940 | 3/1977 | Freyler | 267/153 X |
| 4,473,216 | 9/1984 | Paton et al. | 267/202 |
| 5,114,186 | 5/1992 | Sugiyama | 280/821 |
| 5,460,357 | 10/1995 | Stewart | 267/153 X |

FOREIGN PATENT DOCUMENTS

| | | | |
|---|---|---|---|
| 230754 | 12/1963 | Austria | 267/33 |
| 1553202 | 1/1968 | France | 267/33 |
| 1453093A | 1/1989 | U.S.S.R. | 267/33 |
| 979443 | 1/1965 | United Kingdom | 267/33 |

*Primary Examiner*—Mark T. Le
*Assistant Examiner*—Pamela J. Lipka
*Attorney, Agent, or Firm*—David O'Reilly

[57] ABSTRACT

This invention intends to provide a shock absorbing mechanism for displacement for a stick, an artificial leg etc such as a walking stick, a crutch, a stick for sports, an artificial leg, a walking tool for a patient, a chair, or a protecting bed, in which elastic materials having several different moduli of elasticity are built in a small space of a compression coil spring, and accomplish an elastic sticky force like a human muscle which is light and low in cost.

9 Claims, 9 Drawing Sheets

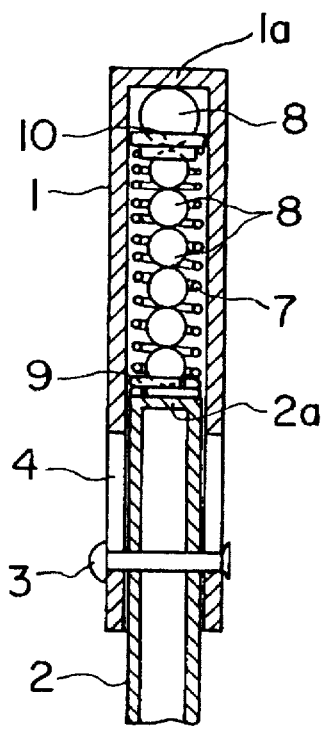
F I G. 2
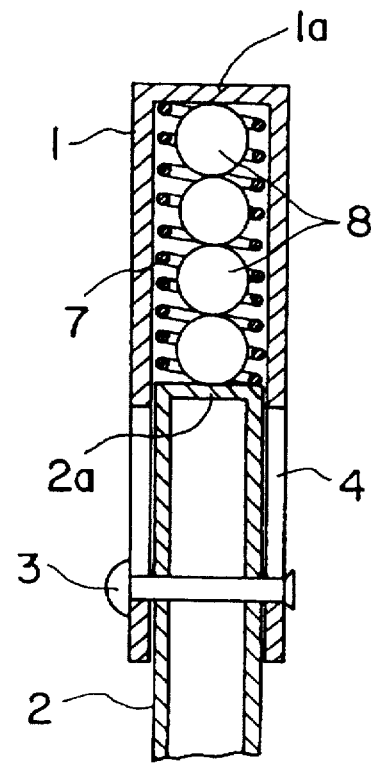
F I G. 4
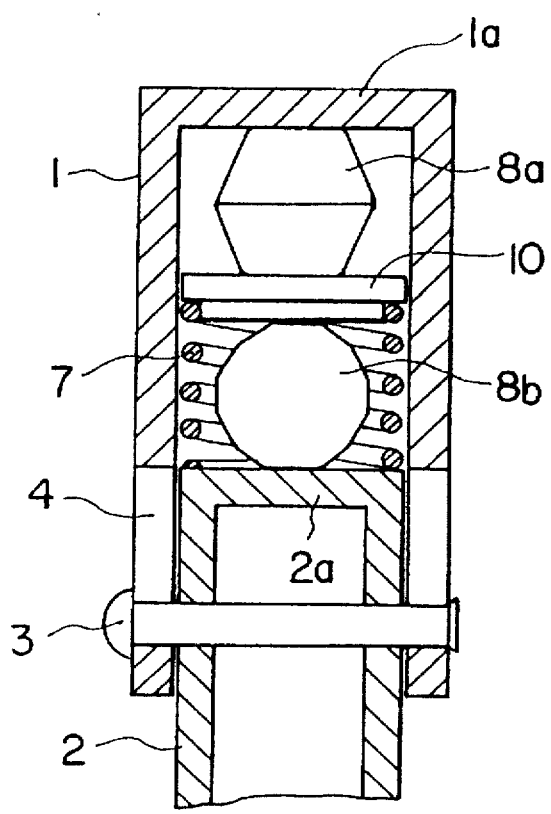
F I G. 3
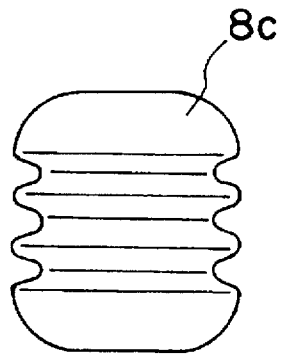
F I G. 5

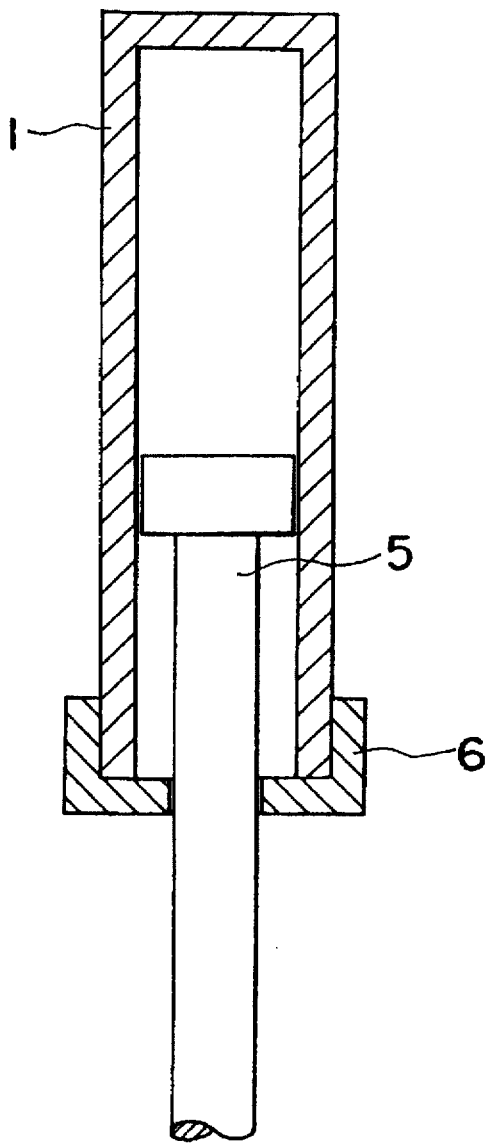
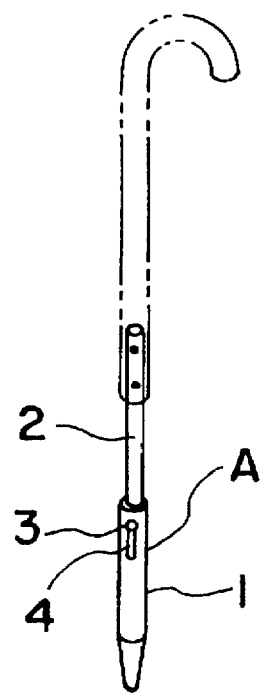
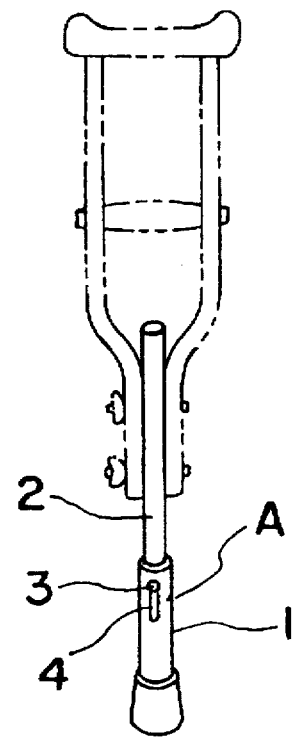
FIG. 8
FIG. 9
FIG. 10

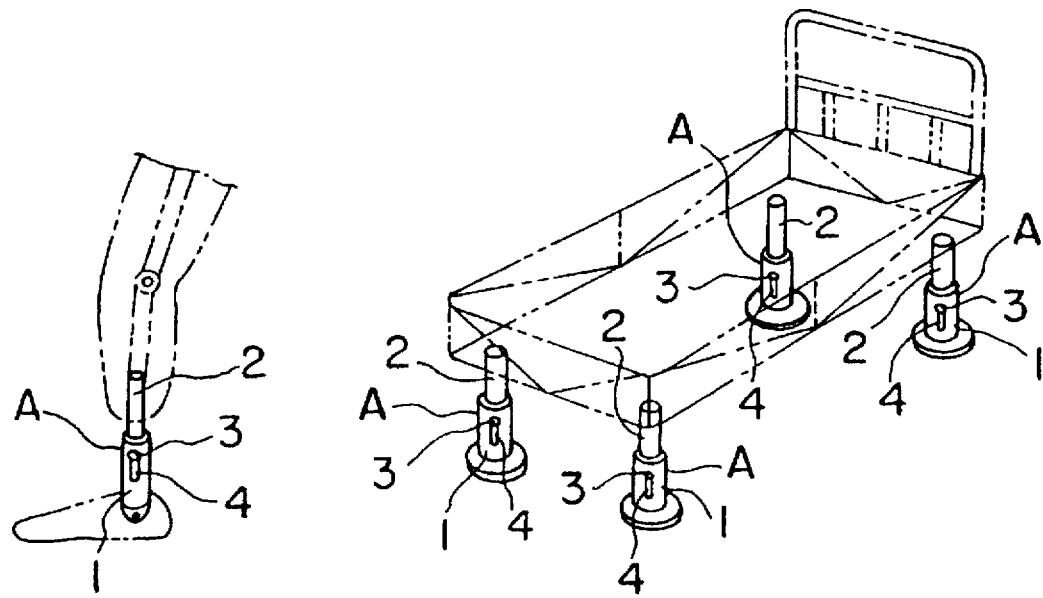
FIG. 11    FIG. 13
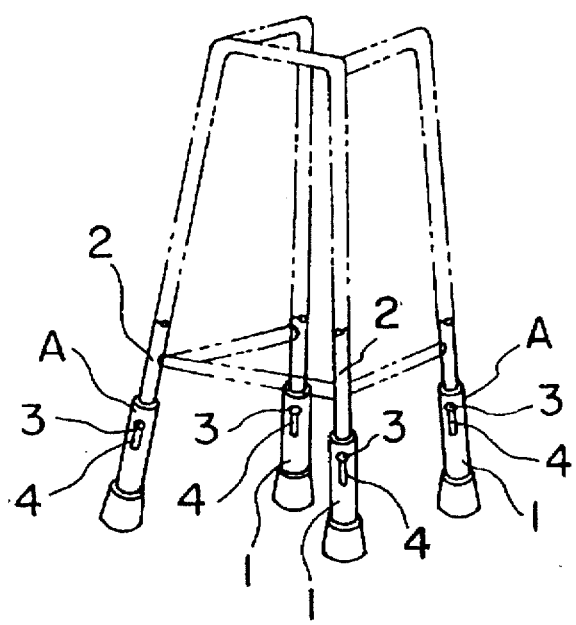 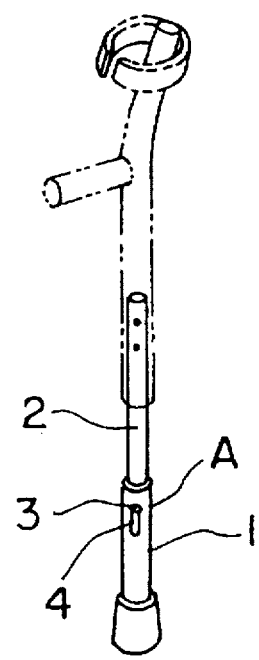
FIG. 12    FIG. 14

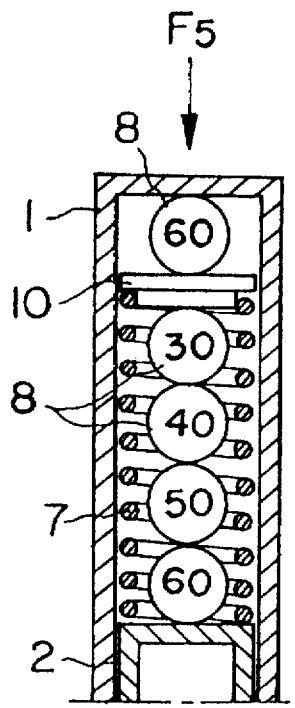
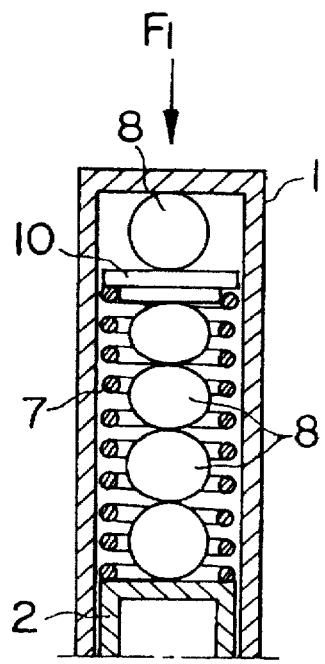
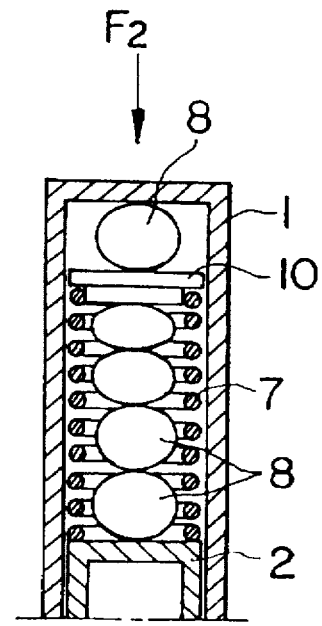
FIG.16(a)　　FIG.16(b)　　FIG.16(c)
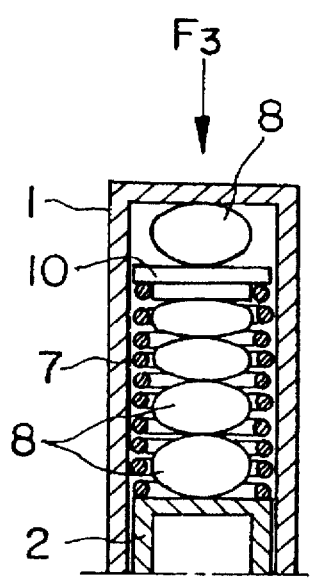
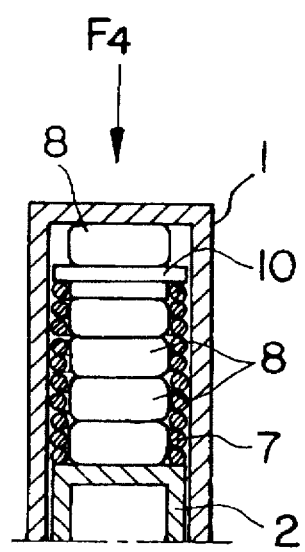
FIG.16(d)　　FIG.16(e)

SHOCK ABSORBING MECHANISM OF DISPLACEMENT FOR STICK, LEG, ETC.

FIELD OF THE INVENTION

This invention relates to a shock absorbing mechanism of displacement for stick, leg etc especially for a shock receiving part of a stick, a crutch, a stick for sports, an artificial leg, a walking tool for a patient, a chair, a protecting bed, a moving bar for supporting body weight, a lofstrand arm crutch, under arm crutch, or other computer, motor, or engine.

BACKGROUND OF THE INVENTION

Prior shock absorbing mechanisms of displacement for a stick, crutch or leg etc uses only one cushion such as coil compression spring, leaf spring, or torsion spring. If the spring force is stiff, the thrust feeling is worse. If the spring force is soft, the spring force yields by the outer force and produces a shock, the thrust feeling is also worse. These drawbacks are by one elastic modulus. For obtaining plural moduli, plural cushions are required at different parts or vicinity, however, the structure is complicated and results in high costs.

The inventor in this application invented the device disclosed in JP Pat pub No 7-10295 and Pat Application No 4-331838.

However, said ski stock of JP Pat pub No 7-10295 has a resilient force of only one elastic modulus. The ski stock of JP Pat Application No 4-331838 and Pub No 7-10295 has an elongate bellows shape elastic cushion inserted in a compression coil spring which bends and interferes with said outer compression coil spring, and a grip body 1 swings against a pipe shaft.

This invention intends to eliminate said drawbacks, and an object of this invention is to provide a shock absorbing displacemant mechanism for a stick, leg etc such as a stick, a crutch, a stick for sports, an artificial leg, a walking tool for a patient, a chair, or a protecting bed.

The other object of this invention is to provide a shock absorbing displacement mechanism for a stick, leg etc in which elastic materials 8, 8, . . . have several kinds of moduli built into the small space of a compression coil spring, and accomplish an elastic sticky force like a human muscle with lightweight and low cost.

The another object of this invention is to provide a ski pole having a reciprocal shock absorbing mechanism in which elastic materials 8, , . . . have several kinds of moduli built into the small space of a compression coil spring, and accomplish an elastic sticky force like a human muscle with light weight and low cost.

The above and other objects, advantages and novel features of this invention will be more fully understood from the following detailed description and the accompanying drawings, in which like reference numbers indicate like or similar parts throughout wherein;

BRIEF DESCRIPTION OF THE INVENTION

This invention comprises an outer sleeve 1 and inner sleeve 2, a compression coil spring 7 being inserted between said outer sleeve 1 and inner sleeve 2, a plurality of elastic materials 8, 8 . . . . such as rubber, plastic being inserted within said compression coil spring 7. A pair of air-tight rings 9, 9 are inserted above an upper end 2a of said inner sleeve 2, a partition plate 10 is inserted between ends 1a and 2a of said outer sleeve 1 and inner sleeve 2, said compression coil spring 7 and elastic materials 8, 8 . . . . are inserted between air-tight ring 9, 9 and partition plate 10, and said elastic materials 8, 8 . . . . are different hardness with respect each other. Further, either one of said outer sleeve 1 or inner sleeve 2 is provided with a three dimensional cam slot 4, the other being provided with a pin 3 inserted into the three dimensional cam slot 4. In this invention, a partition plate 10 is inserted between ends 1a and 2a of said outer sleeve 1 and inner sleeve 2, elastic materials 8, 8 . . . . are inserted between said end 1a and partition plate 10, a compression coil spring 7 and one or more elastic materials 8, 8 inserted between a partition plate 10 and end 2a of inner sleeve 2, said elastic materials 8, 8 . . . . are different hardness with respect to each other. When said outer sleeve 1 and inner sleeve 2 slides with respect to each other and said compression coil spring 7 shrinks, elastic materials 8, 8 . . . . also shrink. Several kinds of modulus are obtained and a soft, strong cushion is achieved. When said compression coil spring 7 shrinks, an inner wall is formed which prevents interference between spring 7 and elastic materials 8, 8 . . . . In the case of a lump of elastic material 8, it collapses in a predetermined space until there is no place left to expand, it does not collapse more than a breaking limit. Therefore, its strength and elasticity are retained for a long time. It is possible to have the effect of preventing shock more than by the combination of a coil spring and oil shock absorber and also have the same effect as an air cushion because said air-tight ring 9, 9 closely contacts inner peripheral face of outer sleeve 1.

This invention also intends to provide a ski pole having a reciprocal shock absorbing mechanism in which a grip body 11 is slidably mounted at an upper part of pipe shaft 13, a cam slot 14, 14a receives a bolt pin 15 inserted into pipe shaft 13, a compression coil spring 16 inserted between the grip body 11 and upper end of the pipe shaft 13, a plurality of elastic materials 17, 17 . . . . such as rubber, plastic inserted within said compression coil spring 16. Said plurality of elastic materials 17, 17 . . . . have a different hardness with respect to each other. An upper part of a pipe shaft 13 provides a shaft head 12 whose outer peripheral surface 12a opposes the inner peripheral face of said grip body 11, said outer peripheral surface 12a having a resilient ring 18 which presses into contact with said inner peripheral face of said grip body 11. Said grip body 11 has recess 20 at a lower end, and a clamp sleeve 21 at the outer of the recess 20 fitted on said recess 20. When grip body 11 slides along pipe shaft 13, bolt pin 15 slides in cam slot 14, 14a and gives a reciprocal and rotational motion to pipe shaft 13, and a reciprocal and thrust action. On the other hand, according to the bending of compression coil spring 16, elastic materials 17, 17 . . . . bend, and an elastic force of several kind of elastic moduli without interference between compression coil spring 16 and elastic materials 17, 17, . . . By clamping clamp sleeve 21 against recess 20 at the lower end of grip body 11, the grip body 11 is stably supported without play in the pipe shaft 13.

BRIEF DESCRIPTION OF THE DRAWINGS

FIG. 2 shows a longitudinal cross section of a second embodiment of this invention.

FIG. 3 shows a longitudinal cross section of a third embodiment of this invention.

FIG. 4 shows a longitudinal cross section of a fourth embodiment of this invention.

FIG. 5 is a side elevation of one configuration for an elastic material used in the invention.

FIG. 8 shows a longitudinal cross section of a seventh embodiment of this invention.

FIG. 9 is an explanatory view of this invention applied to a cane or sport stick.

FIG. 10 is an explanatory view of this invention applied to a patient crutch.

FIG. 11 is an explanatory view of this invention applied to arm artificial leg.

FIG. 12 is an explanatory view of this invention applied to a walking tool for a patient.

FIG. 13 is an explanatory view of this invention applied to a protecting bed.

FIG. 14 is an explanatory view of this invention applied to a lofstrand arm crutch.

FIG. 16($a$) through 16($e$) show the transition states of this invention.

DETAILED DESCRIPTION OF THE INVENTION

Now, referring to FIGS. 1 to 17 of the drawings, the embodiments of a shock absorbing mechanism for a walking stick, an artificial leg etc according to this invention are explained.

Figure 1:
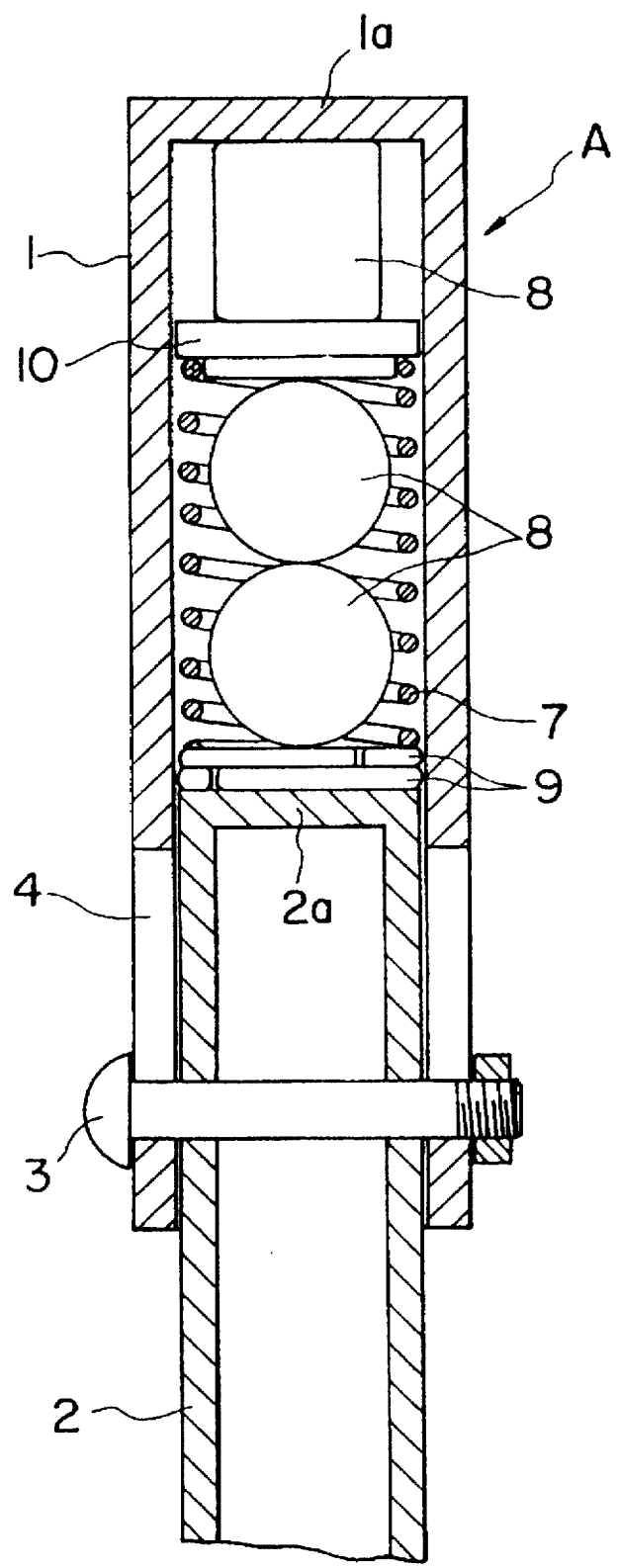
FIG. 1 shows a longitudinal cross section of one embodiment of this invention.

As shown in FIG. 1, the lower part of an outer sleeve 1 is closed at its upper end 1$a$, and an inner sleeve 2, closed at its upper end 2$a$, is slidably mounted, with a pin 3 inserted in the lower part of the inner sleeve 2 engaging three dimensional cam slot 4 provided in outer sleeve 1. A pair of air-tight rings 9, 9 like a piston ring are inserted above an upper end 2$a$ of inner sleeve 2 to offset each recess. A partition plate 10 is inserted between ends 1$a$ and 2$a$ of said outer sleeve 1 and inner sleeve 2. A compression coil spring 7 is inserted between air-tight rings 9, 9 and partition plate 10, and a plurality of elastic materials 8, 8 . . . . such as rubber, plastic are inserted within compression coil spring 7. A similar elastic material 8 is inserted between partition plate 20 and upper end 1$a$ of outer sleeve 1.

Materials 8, 8 . . . . are sphere shape but are not limited to this shape. A plurality of elastic materials 8, 8 . . . . having different hardness to each other may be used. These hardnesses are 60°, 50°, 40°, 30°, 20° respectively.

Operation of the above shock absorbing mechanism is as follows; when outer sleeve 1 slides on sleeve 2, pin 3 also slides in three dimensional cam slot 4, causing compression coil spring 7 to shrink, and elastic materials 8, 8 . . . . to also shrink. As shown in FIG. 16, the softest material 8 deforms firsts and collapses in a predetermined space until there is no spare place, and becomes like a solid. Then the next softer material 8 deforms, and so on, until harder material 8 progressively deforms. Therefore, this cushion is soft initially, then becomes progressively stiffer and stronger. The return motion is in the reverse order, and firmly returns the sleeves to their original position with a soft force. If we change the elastic materials 7 to a material of different hardness, a suitable elastic force according to utility requirement is obtained. Therefore several kind of elastic moduli can be obtained.

Figure 17:
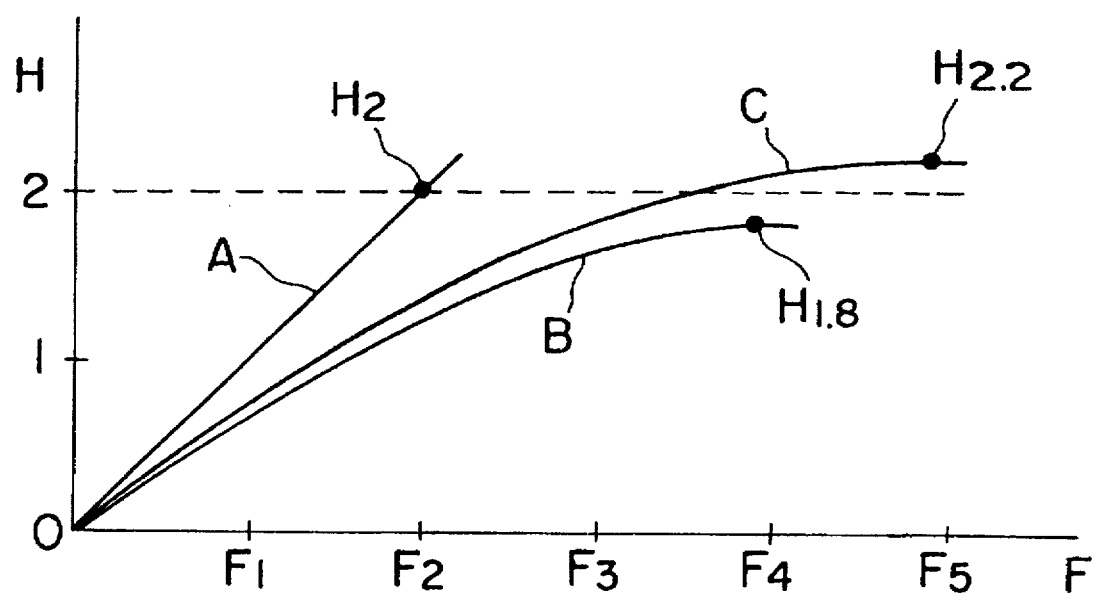
FIG. 17 is a graph of characteristic curves between stress F and strain H.

In FIG. 17, the abscissa shows compression stress F, while the ordinate shows shrink length H. Linear line A shows the characteristic line of only compression coil spring 7, curve B shows the characteristic curve of this invention using elastic materials 8, 8 . . . of different hardness. Total curve achieved by connecting each accumulated energy curve of different hardness becomes a parabola. Range of elasticity limit is increased to $F_4$. Curve C shows a characteristic curve of the embodiment of FIG. 3 in which a partition plate 10 is inserted between ends 1$a$ and 2$a$ of outer sleeve 1 and inner sleeve 2, a hard elastic material 8 is inserted between said end 1$a$ and partition plate 10, the elasticity limit $F_5$ is further increased. As shown in this graph, when compression coil spring 7 shrinks, an inner wall is formed which prevents interference between spring 7 and elastic materials 8, 8 . . . . In the case of a lump of elastic material 8, it collapses in a predetermined space until no room is left, it does not collapse more than the breaking limit. Therefore, it is possible to have an effect that is more than a coil spring and an oil shock absorber and to have an elastic sticky force like a human muscle which is suitable for an artificial hand, leg etc. It is possible to have an effect for preventing shock that is more than a coil spring and an oil shock absorber and to have the same effect as an air cushion.

FIG. 2 shows second embodiment of this invention with the same numerals used for the same parts in the preceding embodiment and only the different parts are explained. FIG. 2 uses 6 spheres of elastic materials 8, 8 . . . . on air-tight rings 9, 9. In this case, the elastic force has more moduli.

FIG. 3 shows a third embodiment of this invention with the same numerals used for the same parts the in preceding embodiment and only the different parts are explained. FIG. 3 uses double frustum conical elastic material 8$a$ inserted above partition plate 10, and only one elastic materials 8$b$ inserted in compression coil spring 7.

FIG. 4 shows a fourth embodiment of this invention with the same numerals used for the same parts in the preceding embodiment and only the different parts are explained. FIG. 4 inserts compression coil spring 7 and 4 spheres of elastic materials 8 between ends 1$a$ and 2$a$ of outer sleeve 1 and inner sleeve 2.

Elastic materials 8 in the fourth embodiment may be elastic materials 8$c$ as shown in FIG. 5 having a plurality of annular grooves in its peripheral face. By this configuration, it is possible to obtain an elastic force of plural moduli.

Figure 6:
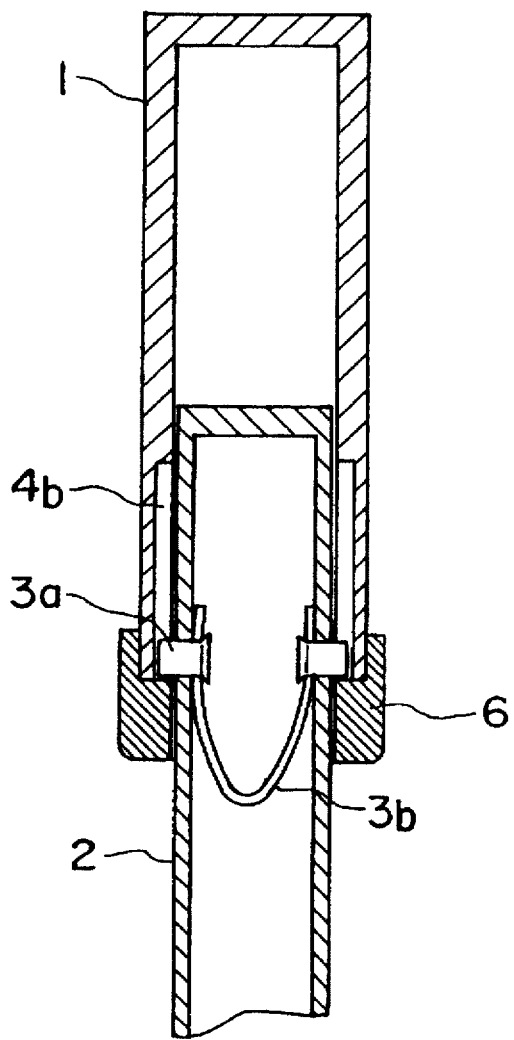
FIG. 6 shows a longitudinal cross section of a fifth embodiment of this invention.
Figure 7:
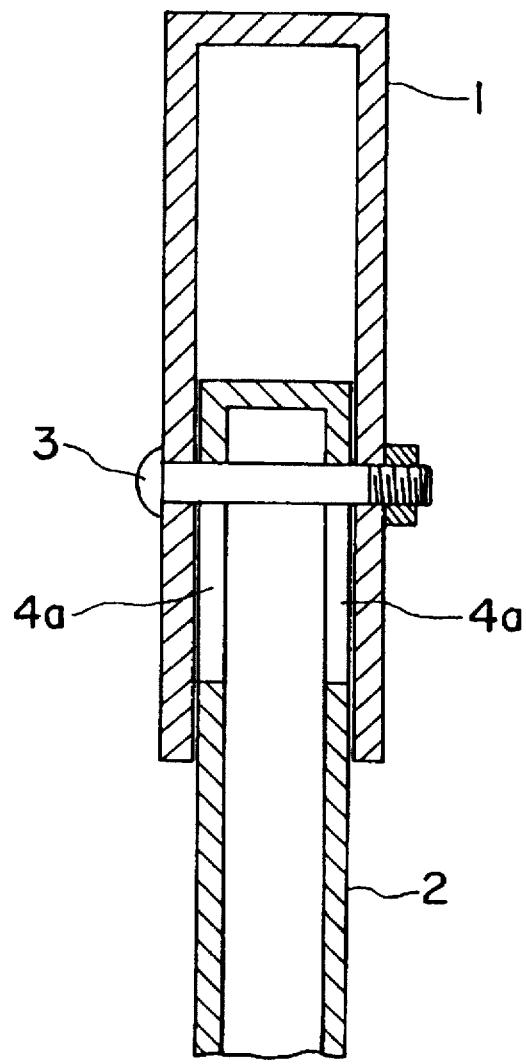
FIG. 7 shows a longitudinal cross section of a sixth embodiment of this invention.

In the preceding the embodiments, three dimensional cam slot 4 is provided in outer sleeve 1, but this three dimensional cam slot 4 may be inner groove 4$b$ provided in inner peripheral face of outer sleeve 1 as shown in FIG. 6 or a cam slot 4$a$ provided on inner sleeve 2 as shown in FIG. 7. In the preceding embodiments, pin 3 passes through inner sleeve 2 but it may be a pair of pins 3$a$, 3$a$ biased outwardly by U shaped spring 3$b$.

In the preceding the embodiments, a three dimensional cam slot 4 is provided in outer sleeve 1, and pin 3 is provided in inner sleeve 2, but this relation is arbitrary. As shown in FIG. 6, inner sleeve 2 provides recesses 4b, 4b of three dimensional cam slot 4, and pins 3a pass through holes in inner sleeve 2 into recesses 4b, 4b in outer sleeve 1. A cap 6 is provided on outer sleeve 1.

As shown in FIG. 8, outer sleeve 1 and piston 5 are employed instead of pin 3 and three dimensional cam slot 4, a cap 6 is provided at a lower end of outer sleeve 1 to prevent the escapement of piston 5.

FIGS. 9, 10, 11, 12, 13 show 6 applications of shock absorbing mechanism A of this invention, FIG. 9 shows a walking stick, or a stick for sports, FIG. 10 shows patient crutch, FIG. 11 shows an artificial leg, FIG. 12 shows a walking tool for a patient, FIG. 13 shows a protecting bed.

Figure 15:
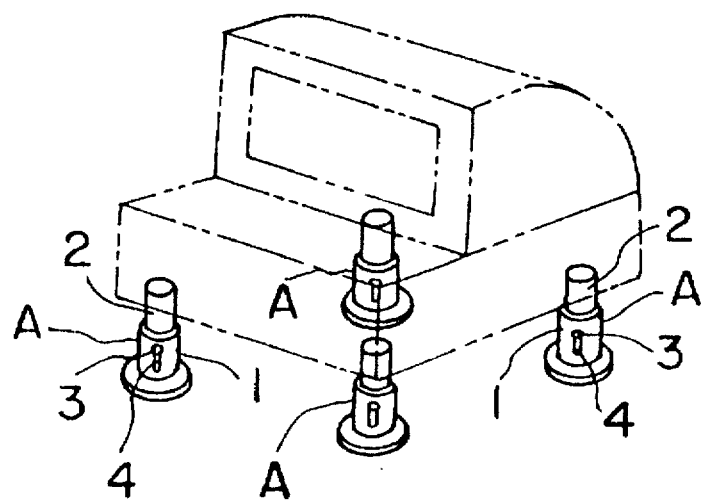
FIG. 15 is an explanatory view of this invention applied to a carrying device for electronic machines and instruments, motors, engine, or seats of a vehicle.

FIG. 14 shows a lofstrand or arm crutch, and FIG. 15 shows a carrying device or enclosure for electronic machines and instruments, a motor, an engine, or seat of a vehicle.

As explained above, according to this invention, it is possible to obtain several kind of moduli by a simple construction, a soft and strong cushion which can not obtained by a single spring, which is more effective to prevent shock than an oil shock absorber, and provides a sticky elastic force like a human muscle. The return movement is not a rapid reflection but is also soft and firmly returns to the original position. At this moment, the elastic material does not interfere with compression coil spring 7. In the case of a lump of elastic material 8, it collapses in a predetermined space until no room is left but it does not collapse more than the breaking limit. Therefore, its strength and elasticity are retained for a long time. It is possible to have the same effect as an air cushion because air-tight ring 9, 9 closely contacts inner peripheral face of outer sleeve 1. By mounting inner sleeve 2 at the lower part of outer sleeve 1, they are stably supported without play with respect to each other. But their relation may be reversed. The inner sleeve 2 may have a compression coil spring 7 and plurality of elastic material 8, 8, . . .

Now, referring to drawings of FIGS. 18 to 22, embodiments of ski pole according to this invention are explained.

Figure 18:
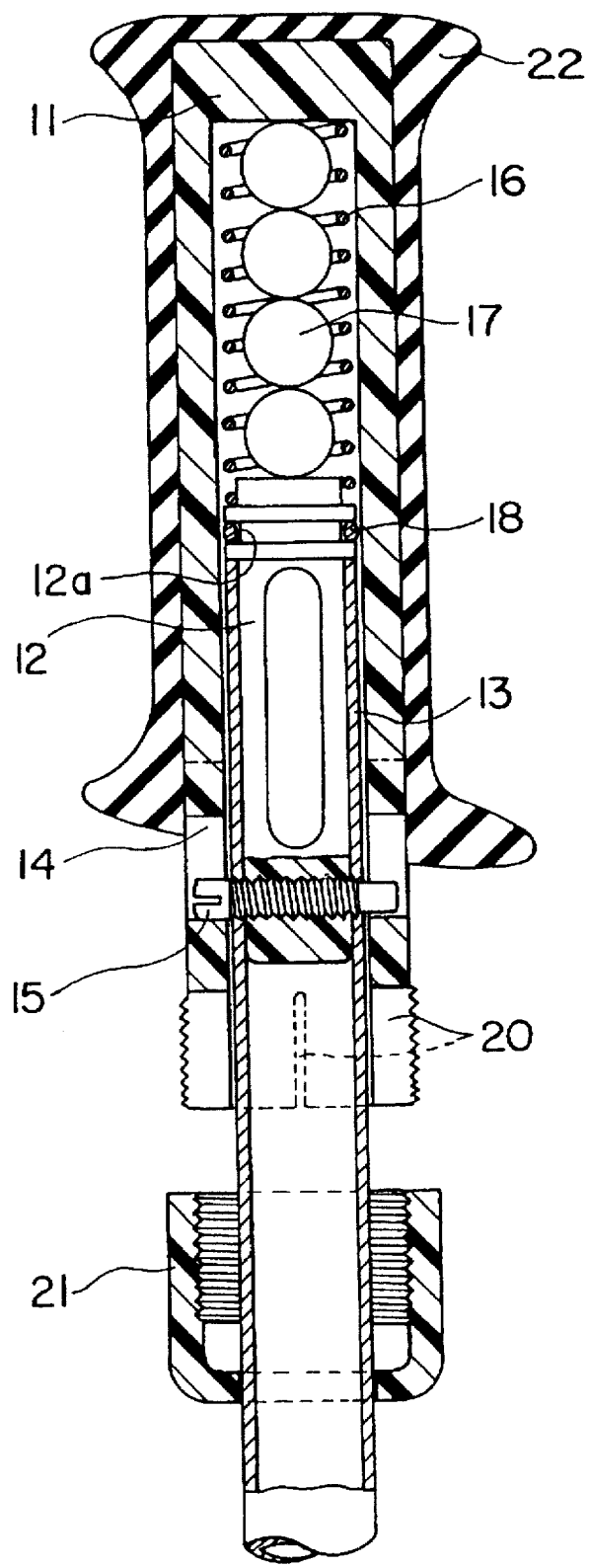
FIG. 18 is a longitudinal cross section of an eighth embodiment of this invention.
Figure 19A:
FIG. 19 ($a$), ($b$), ($c$), ($d$), shows four examples of resilient ring 18.
Figure 19B:
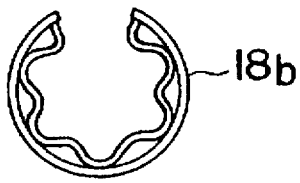
Figure 19C:
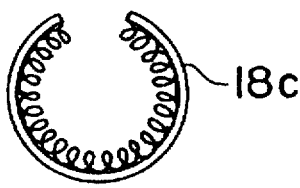
Figure 19D:
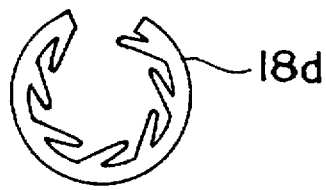

As shown in FIG. 18, a grip body 11 of resilient materials closed at its upper end is slidably mounted at upper part of pipe shaft 13, two three dimensional cam slots 14, 14 receive a bolt pin 15 inserted in pipe shaft 13. Compression coil spring 16 is inserted between grip body 11 and upper end of pipe shaft 13. A plurality of elastic materials 17, 17 . . . . such as rubber, plastic are inserted within said compression coil spring 16. A grip part 22 is mounted on the outer side of grip body 11.

Elastic material 17, 17 . . . . are spherical shaped but are not limited to this shape. The plurality of elastic materials 17, 17 . . . . have different hardness than each other. These hardness are 60°, 50°, 40°, 30°, 20° respectively.

Figure 20:
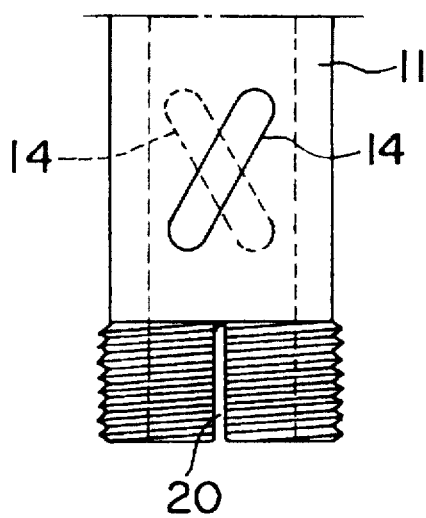
FIG. 20 is a side view of three dimensional cam slot 4 of the embodiment.

As shown in FIG. 20, three dimensional cam slots 14, 14 are grooves extending helically and give a rotational thrust movement to pipe shaft 13.

An upper part of pipe shaft 13 provides shaft head 12 whose outer peripheral surface 12a opposes the inner peripheral face of grip body 11. Outer peripheral surface 12a has a resilient ring 18 which presses in contact with said inner peripheral face of grip body 11. Grip body 11 has recess 20 at a lower end, and a clamp sleeve 21 at the outer portion of recess 20 slidably fits on recess 20.

Shaft head 12 comprises a small diameter part inserted into pipe shaft 13 and a large diameter part for abutting the upper end of pipe shaft 13. Annular recess for fitting resilient ring 18 is provided on said large diameter part. Bolt pin 15 passes through shaft head 12 and projects through the opposite side of pipe shaft 13 and the projecting part engage cam slots 14, 14.

Operation of this ski pole is as follows; When grip body 11 slides along pipe shaft 13, bolt pin 15 slides in helical three dimensional cam slot 14, 14 and gives a thrusting rotational motion to pipe shaft 13, and a reciprocal thrust action. On the other hand, according to the bending of compression coil spring 16, elastic materials 17, 17 . . . progressively bend from the soft one to the harder one. If we change to elastic materials 17 of different hardness, a suitable elastic force is obtained. Therefore several kinds of elastic moduli can be obtained. Because elastic material 17, collapses in a space and no space is left, it acts an as oil shock absorber to prevent shock.

When clamp sleeve 21 is fitted on lower end of grip body 11, the inner face of grip body 11 contacts the outer face of pipe shaft 13, grip body 11 is stably supported without any play in pipe shaft 13.

FIGS. 19 (a), (b), (c), (d), shows four examples of a resilient ring 18. FIG. 19 (a) shows a simple split ring 18a. Resilient ring 18b of consists of a simple split ring and a wave spring inside thereof. Resilient ring 18c uses a coil spring instead of the wave spring in resilient ring 18b. The simple split ring and a wave spring inside thereof in resilient ring 18d is formed by a single wire.

These resilient rings 18 form an air tight contact with the inner face of grip body 11 and have the same effect as an air cushion.

Figure 21:
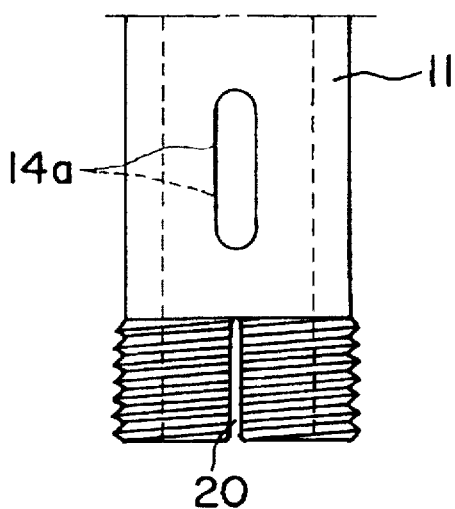
FIG. 21 is a side view of longitudinal cam slot 4$a$ of another embodiment.

FIG. 21 shows another embodiment of this invention, in which longitudinal cam slots 14a are employed instead of three dimensional cam slot 14.

In this embodiment, when said grip body 11 slides along pipe shaft 13, bolt pin 15 slides in longitudinal cam slot 14a and gives a reciprocal action motion to pipe shaft 13.

Figure 22:
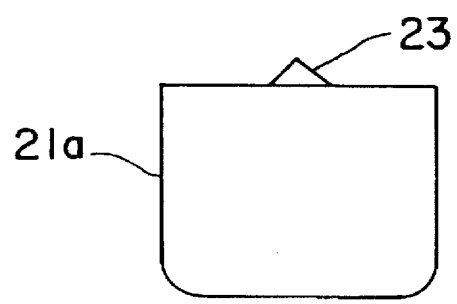
FIG. 22 is a side view of clamp sleeve 11$a$ of still another embodiment.

FIG. 22 shows still another embodiment of clamp sleeve 21a having triangular projection 23, 23 at its upper face. By this projection 23, 23 pierces lower face of grip part 22, to prevent it from loosening.

As explained above, in this invention, it is possible to obtain several kinds of elastic moduli by a simple construction and without interference between compression coil spring 16 and elastic materials 17, 17 . . . . And, by clamping clamp sleeve 21 against recess 20 at the lower end of grip body 11, grip body 11 is stably supported without any play in pipe shaft 13 together with the co-operation of resilient rings 18 in air tight contact with the inner face of grip body 11.

What we claim is:

1. A shock absorbing mechanism for displacement for a stick, an artificial leg and the like comprising; an outer sleeve (1); and an inner sleeve (2), a compression coil spring (7) inserted between said outer sleeve (1) and inner sleeve (2); a plurality of elastic materials (8) of rubber or plastic inserted within said compression coil spring 7; a pair of airtight rings (9) inserted above an upper end (2a) of said inner sleeve (2); a partition plate (10) inserted between respective inner ends (1a and 2a) of said outer sleeve (1) and inner sleeve (2); said compression coil spring (7) with said elastic materials (8) being inserted between said airtight ring (9) and said partition plate (10); said elastic materials (8) being different in hardness to each other.

2. A shock absorbing mechanism according to claim 1 in which either of said outer sleeve (1) or inner sleeve (2) is provided with a three dimensional cam slot (4), the other being provided with a pin (3) inserted into the three dimensional cam slot (4).

3. A shock absorbing mechanism according to claim 1, including one or more elastic materials (8) inserted between said end of said outer sleeve (1a) and said partition plate (10).

4. A shock absorbing mechanism for a walking stick, crutch or the like comprising: an outer sleeve (1); an inner sleeve (2) slidably fitting into said outer sleeve (1); a compressible coil spring (7) fitting inside said outer sleeve above an end of said inner sleeve; one or more resilient inserts (8) inside said compressible coil spring (7); a partitioning plate (10) partitioning a space between said compressible coil spring (7) and an end of said outer sleeve; at least one resilient elastic insert (8) between said partitioning plate (10) and said end of said outer sleeve (1); and one or more airtight resilient rings (9) between an inner end of said inner sleeve (2) and said compressible spring (7); said compressible coil spring (7) and said one or more resilient inserts (8) being compressed when said inner sleeve (2) slides in said outer sleeve (1).

5. The mechanism according to claim 4 in which said one or more resilient inserts (8) inside said compressible coil spring (7) each have a different modulus of elasticity.

6. The mechanism according to claim 5 in which said at least one resilient elastic insert between said partition plate and an end of said outer sleeve has a different modulus of elasticity than said one or more resilient inserts.

7. The mechanism according to claim 6 including a cam slot (4) in either said outer sleeve (1) or said inner sleeve (2); and a bolt (3) passing through said cam slot and both said inner sleeve (2) and outer sleeve (1) to hold said inner sleeve (2) in said outer sleeve (1).

8. The mechanism according to claim 4 in which said one or more resilient inserts (8) inside said compressible coil spring (7) each have a different modulus of elasticity.

9. The mechanism according to claim 8 in which said at least one resilient elastic insert (8) between said partition plate (10) and an end of said outer sleeve (2) has a different modulus of elasticity than said one or more resilient inserts (8).

* * * * *